(12) United States Patent
Cole et al.

(10) Patent No.: US 6,613,729 B1
(45) Date of Patent: Sep. 2, 2003

(54) WET WIPES CONTAINING CATIONIC FATTY ACID SURFACTANTS

(75) Inventors: Douglas Bryan Cole, Hortonville, WI (US); Katherine Denise Stahl, Appleton, WI (US); Rhonda Sue Solberg, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/560,071

(22) Filed: Apr. 27, 2000

(51) Int. Cl.[7] .................... C11D 17/04; C11D 1/62; A61K 7/48
(52) U.S. Cl. .................. 510/405; 510/108; 510/130; 510/143; 510/433; 510/439; 510/504; 424/402
(58) Field of Search .................. 510/130, 143, 510/108, 439, 433, 405, 504; 424/402

(56) References Cited

U.S. PATENT DOCUMENTS

| | | | |
|---|---|---|---|
| 4,100,324 A | 7/1978 | Anderson et al. | 428/288 |
| 4,533,545 A | 8/1985 | Sebag | 424/70 |
| 4,673,525 A | 6/1987 | Small et al. | |
| 4,812,253 A | 3/1989 | Small et al. | |
| 5,078,990 A | 1/1992 | Martin et al. | 424/70 |
| 5,096,608 A | 3/1992 | Small et al. | |
| 5,188,756 A * | 2/1993 | Baker et al. | 510/159 |
| 5,194,252 A * | 3/1993 | Hofmann | 424/73 |
| 5,256,417 A | 10/1993 | Koltisko | 424/402 |
| 5,300,242 A | 4/1994 | Nichols et al. | 508/460 |
| 5,366,732 A * | 11/1994 | Zighelboim | 424/411 |
| 5,443,757 A | 8/1995 | Brumbaugh | 510/237 |
| 5,620,527 A * | 4/1997 | Kramer et al. | 134/2 |
| 5,783,146 A * | 7/1998 | Williams, Jr. | 422/26 |
| 5,904,810 A | 5/1999 | Schroeder et al. | 162/111 |
| 5,935,384 A * | 8/1999 | Taniguchi | 162/172 |
| 5,945,093 A | 8/1999 | Duvel | 424/70.12 |
| 5,997,890 A | 12/1999 | Sine et al. | 424/401 |
| 6,013,615 A * | 1/2000 | Zhou et al. | 510/434 |
| 6,120,644 A * | 9/2000 | Schroeder et al. | 162/158 |
| 6,136,884 A * | 10/2000 | Chen et al. | 523/105 |
| 6,153,208 A * | 11/2000 | McAtee et al. | 424/402 |
| 6,211,140 B1 * | 4/2001 | Sivik et al. | 510/515 |
| 6,217,889 B1 * | 4/2001 | Lorenzi et al. | 424/401 |
| 6,322,801 B1 * | 11/2001 | Lorenzi et al. | 424/402 |

FOREIGN PATENT DOCUMENTS

| | | |
|---|---|---|
| EP | EP 0 875 233 A1 | 11/1998 |
| GB | 2143249 A * | 2/1985 |
| WO | WO 95/31189 | 11/1995 |
| WO | WO-95/31189 A1 * | 11/1995 |
| WO | WO 97/30217 A1 | 8/1997 |
| WO | WO-97/30217 A1 * | 8/1997 |
| WO | WO 99/24551 A1 | 5/1999 |
| WO | WO 00/65911 A1 | 9/2000 |

* cited by examiner

*Primary Examiner*—Lorna M. Douyon
(74) *Attorney, Agent, or Firm*—Gregory E. Croft; Michael J. Bendel

(57) ABSTRACT

Wet wipes impregnated with an aqueous solution containing cationic fatty acid surfactants provide improved tactile properties and cleaning efficacy without excessive skin irritation or foaming when compared to conventional wet wipes.

12 Claims, No Drawings

WET WIPES CONTAINING CATIONIC FATTY ACID SURFACTANTS

BACKGROUND OF THE INVENTION

Wet wipes are well known commercial consumer products which have been available in many forms. Perhaps the most common form of wet wipes has been a stack of moistened sheets which have been packaged in a plastic container. The wet wipes have been made from a variety of materials which have been moistened with a variety of suitable wiping solutions. Typically, the wet wipes have been available in either folded or unfolded configurations. For example, stacks of wet wipes have been available wherein each of the wet wipes in the stack has been arranged in a folded configuration such as a c-folded, z-folded or quarter-folded configuration as are well known to those skilled in the art. Each folded wet wipe has also been interfolded with the wet wipes immediately above and below in the stack of wet wipes. In an alternative configuration, the wet wipes have been in the form of continuous webs of material which include perforations to separate the individual wet wipes and which are wound into rolls and packaged in plastic containers.

Such wet wipes have been used for baby wipes, hand wipes, household cleaning wipes, industrial wipes and the like.

The solutions incorporated into conventional wet wipes have usually included a number of ingredients intended to enhance or impart particular properties to the wipe. These properties have related to, for example, cleaning efficacy, fragrance, medication, reduced irritation, skin health, aesthetics of the product and the like. For baby wipes in particular, a solution providing a gentle soothing feeling without excessive irritation or foam while maintaining cleaning and preservation efficacy is highly desirable for product performance. Suitable ingredients used to provide such properties have included water, emollients, surfactants, preservatives, chelating agents, pH buffers, fragrance or combinations thereof. The solutions have also contained lotions and/or medicants.

However, the conventional solutions and, in particular, the surfactants in such solutions for wet wipes have not been completely satisfactory. For example, to reduce the level of skin irritation, conventional wet wipe solutions have included amphoteric surfactants which generally cause little or no skin irritation. Such amphoteric surfactants have included sodium cocoamphoacetate and disodium cocoamphodiacetate. However, such amphoteric surfactants have typically not exhibited the high levels of cleaning efficacy associated with other surfactants such as anionic surfactants. Such amphoteric surfactants typically have also not provided the optimum silky feeling to the skin which is desired by consumers.

On the other hand, anionic surfactants, while exhibiting such cleaning efficacy, have generally caused excessive skin irritation such as dryness and scaling and, as a result, have not been suitable for use in wet wipe applications. The high level of skin irritation caused by such surfactants is particularly undesirable in baby wipe applications due to the tenderness of the infants skin. Moreover, most anionic surfactants are suitable for detergent compositions due to their high levels of foaming and detersive activity. However, such foaming is generally undesirable in wet wipe applications and, in particular, in baby wipe applications. Consumers who use wet wipes prefer that the solution from the wet wipes not leave any soapy or bubbly residue on the surface of the skin since the solution is usually not wiped off the skin after the wet wipe is used.

Accordingly, it remains desirable to provide solutions for wet wipes which include surfactants which exhibit improved cleaning efficacy while not causing excessive skin irritation or foaming while leaving the skin with silky or powdery tactile properties.

SUMMARY OF THE INVENTION

It has now been discovered that certain cationic surfactants can impart improved skin glide, improved moisture perception, and provide a soft, powdery or talc-like feel to the skin when used in a wet wipe solution formulation.

Hence, in one aspect, the invention relates to a wet wipe comprising a fibrous sheet material and an aqueous solution, said solution containing from about 0.01 to about 20 weight percent of a cationic fatty acid surfactant having a fatty acid moiety carbon chain length of from 8 to 40 carbon atoms.

In another aspect, the invention resides in an aqueous solution containing from about 0.01 to about 20 weight percent of a cationic fatty acid surfactant having a fatty acid moiety carbon chain length of from 8 to 40.

Suitable fatty acid moieties include, without limitation, oils from sunflower seed, silk, wheat germ, coconut, soy, rice, olive and almond.

Particular suitable cationic surfactants include sunflower seedamidopropyl morpholine lactate, sunflower seedamidopropyl morpholine malate, isostearamidopropyl dimethylamine lactate, and isostearylamidopropyl dimethylamine malate. Their structures are set forth below:

Sunflower Seedamidopropyl Morpholine Malate

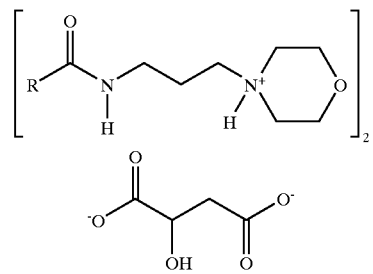

wherein RC(O) is the acyl group derived from sunflower seed oil fatty acids.

Sunflower Seedamidopropyl Morpholine Lactate

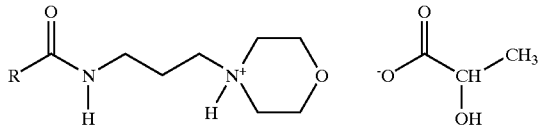

wherein RC(O) is the acyl group derived from sunflower seed oil fatty acids.

Isostearamidopropyl Dimethylamine Lactate

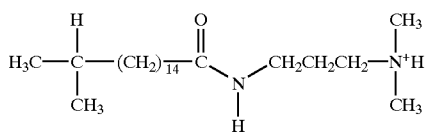

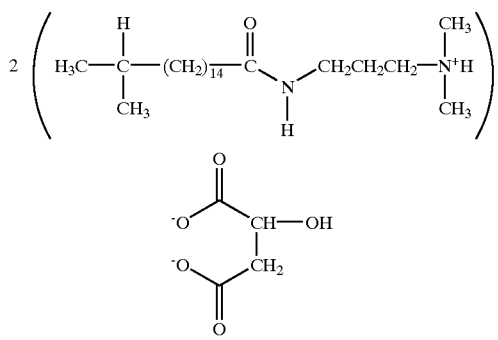

Isostearamidopropyl Dimethylamine Malate

The amount of the fatty acid cationic surfactant in the aqueous solution can be from about 15 0.01 to about 20 weight percent, more specifically from about 0.1 to about 10 weight percent, and still more specifically from about 0.1 to about 5 weight percent.

In another aspect, the abovesaid cationic fatty acid surfactants can be combined with nonionic surfactants to further improve the performance of the solution. Suitable nonionic surfactants include sorbitan fatty acid esters having a fatty acid moiety carbon chain length of from 12 to 18 combined with ethylene oxide of 10–100 molar ratio. Specific examples of suitable nonionic surfactants include sorbitan monolaurate, sorbitan monoisostearate, sorbitan monopalmitate, lauramidodiethanolamide, isostearamidediethanolamide, alcohol ethoxylates, alkylphenol ethoxylates and combinations thereof.

The amount of the nonionic surfactant in the aqueous solution can be from about 0.1 to about 5 weight percent, more specifically from about 0.1 to about 3 weight percent, and still more specifically from about 0.1 to about 1 weight percent.

DETAILED DESCRIPTION OF THE INVENTION

The present invention relates to fibrous materials and, in particular, wet wipes which have improved cleaning efficacy without excessive skin irritation or foaming. The wet wipes of the present invention can be used for baby wipes, hand wipes, face wipes, cosmetic wipes, household wipes, industrial wipes and the like. Such wet wipes are generally folded and arranged in a stacked configuration inside a suitable container for consumer sale.

Materials suitable for such wet wipes are well known to those skilled in the art. The wet wipes are typically made from fibrous sheet materials which may be woven or nonwoven. For example, the wet wipes of the present invention may include nonwoven fibrous sheet materials which include meltblown, coform, air-laid, bonded-carded web materials, hydroentangled materials, combinations thereof and the like. Such materials can comprise synthetic or natural fibers or combinations thereof. Typically, the wet wipes define a basis weight of from about 25 to about 120 grams per square meter and desirably from about 40 to about 90 grams per square meter.

In a particular aspect, the wet wipes of the present invention comprise a coform basesheet of polymeric microfibers and cellulosic fibers having a basis weight of from about 60 to about 80 grams per square meter and desirably about 75 grams per square meter. Such coform basesheets are manufactured generally as described in U.S. Pat. No. 4,100,324 to Anderson et al. which issued Jul. 11, 1978, and which is herein incorporated by reference. Typically, such coform basesheets comprise a gas-formed matrix of thermoplastic polymeric meltblown microfibers, such as, for example, polypropylene microfibers, and cellulosic fibers, such as, for example, wood pulp fibers.

The relative percentages of the polymeric microfibers and cellulosic fibers in the coform basesheet can vary over a wide range depending on the desired characteristics of the wet wipes. For example, the coform basesheet may comprise from about 20 to about 100 weight percent, desirably from about 20 to about 60 weight percent, and more desirably from about 30 to about 40 weight percent of polymeric microfibers based on the dry weight of the coform basesheet being used to provide the wet wipes.

Alternatively, the wet wipes of the present invention can comprise a composite which includes multiple layers of materials. For example, the wet wipes may include a three layer composite which includes an elastomeric film or meltblown layer between two coform layers as described above. In such a configuration, the coform layers may define a basis weight of from about 15 to about 30 grams per square meter and the elastomeric layer may include a material such as a metallocene polyethylene.

The individual wet wipes are generally arranged in a folded configuration. Such folded configurations are well known to those skilled in the art and include c-folded, z-folded, quarter-folded configurations and the like. Each wet wipe may also be interfolded with the wet wipes immediately above and below in the stack of wet wipes. The wet wipes generally define an unfolded width and an unfolded length. The wet wipes may have any suitable unfolded width and length. For example, the wet wipes may have an unfolded length of from about 2.0 to about 80.0 centimeters and an unfolded width of from about 2.0 to about 80.0 centimeters.

The wet wipes of the different aspects of the present invention also contain a solution which is absorbed into the wet wipes. The amount of solution contained within each wet wipe may vary depending upon the type of material being used to provide the wet wipe, the type of solution being used, the type of container being used to store the wet wipes, and the desired end use of the wet wipes. Generally, each wet wipe can contain from about 150 to about 600 weight percent and desirably from about 250 to about 450 weight percent solution based on the dry weight of the wipe for improved wiping. In a particular aspect, wherein the wet wipes are made from a coform material comprising from about 30 to about 40 weight percent polymeric microfibers based on the dry weight of the wipe, the amount of solution contained within the wet wipe is from about 300 to about 400 weight percent and desirably about 330 weight percent based on the dry weight of the wet wipe. If the amount of solution is less than the above-identified range, the wet wipe may be too dry and may not adequately perform. If the amount of solution is greater than the above-identified range, the wet wipe may be oversaturated and soggy and the solution may pool in the bottom of the container.

The solution contained within the wet wipes of the present invention defines a pH from about 5 to about 8 and desirably from about 5 to about 6. A pH level below about 5 and a pH level greater than about 8 are undesirable and can lead to skin irritation.

The solution may also include a variety of other components which may assist in providing the desired wiping and cleaning properties. For example, the components may include water, emollients, other surfactants, preservatives, chelating agents, pH buffers, fragrances or combinations thereof. The solution may also contain lotions and/or medicants. To provide reduced skin irritation, the solution desirably includes at least about 80 weight percent water and more desirably at least about 90 weight percent water based on a total weight of the solution.

For example, the solution may include an effective amount of preservative to inhibit the growth of microorganisms. Suitable preservatives are well known to those skilled in the art and may include, for example, parabens, sodium hydroxymethylglycinate, organic acids such as benzoic and malic acid, DMDM hydantoin and the like and combinations thereof. In a particular embodiment, the preservative is sodium hydroxymethylglycinate which is commercially available from Sutton Laboratories under the trade designation SUTTOCIDE A. The solution may include any amount of the preservatives which provides the desired antimicrobial effect. For example, the solution may include from about 0.1 to about 1.0 weight percent of the preservative based on a total weight of the solution.

The solution may further include additional surfactants which can act as an emulsifier or co-solvent or co-detergent that mitigates the irritation potential of an ionically charged primary surfactant. Suitable cosurfactants include, for example, anionic surfactants such as monoalkyl phosphates, acyl glutamates and acyl isethionates, alkanolamids, amphoteric surfactants, nonionic surfactants and the like or combinations thereof. For example, a suitable acyl glutamate anionic surfactant is potassium cocyl glutamate, a suitable acyl isethionate anionic surfactant is ammonium cocyl isethionate, and suitable amphoteric surfactants include disodium capryloamphdipropionate and disodium cocoamphodiacetate. Suitable nonionic surfactants include diethanolamides having an average of from 12 to 16 carbon atoms, alkylphenol ethoxylates, alcohol ethoxylates, sorbitan fatty acid esters, glycerol fatty acid esters and the like. The solution may include any amount of the cosurfactant which provides improved mildness, cleaning, foam reduction or tactile properties. For example, the solution may include from about 0.01 to about 5 weight percent of the cosurfactant based on a total weight of the solution.

In a particular embodiment, the solution of the present invention includes from about 0.01 to about 5.0 and desirably from about 0.1 to about 1.0 weight percent of a nonionic surfactant commercially available from Rhodia, Inc. under the trade designation ALKAMULS PSML-20. The addition of such a cosurfactant provides reduced skin irritation and reduced foaming. Such a cosurfactant also acts as an coemulsifier in conjunction with the cationic fatty acid surfactant.

In another specific embodiment, it has been discovered that the addition of certain cosurfactants such as Lauramide DEA or Cocoamide DEA may provide a broader range of acceptable pH. For example, the addition of Lauramide DEA allowed the acceptable pH range to expand from a range of 6.5 to 8 to a range of from about 5 to about 8. Such an expansion of the acceptable pH range provides improved processability and provides a clear, homogeneous solution. For example, the solution may include Lauramide DEA which is commercially available from Rhodia, Inc. under the trade designation ALKAMIDE LE. Such a solution may include from about 0.01 to about 5.0 and desirably from about 0.1 to about 1.0 weight percent of said cosurfactant based on a total weight of the solution.

The wet wipes of the different aspects of the present invention may be manufactured using several different processes well known to those skilled in the art. The particular method and sequence of steps described herein is not a limitation to the present invention, but is disclosed only as one method of producing a wet wipe and stack of wet wipes. Initially, a supply roll of the material being converted into the wet wipes is unwound to provide a continuously moving web of material. The web of material is saturated or otherwise impregnated with the solution of the present invention by any suitable means such as spraying, dipping, or the like as are well known to those skilled in the art. In a particular aspect, the web of material is passed over several perforated tubes which exude the solution into the material.

The web of material is slit in the machine direction into multiple ribbons, each of which may be folded into the type of fold desired for the individual wet wipe. The web of material is slit using a cutter as are well known to those skilled in the art. For example, the web of material can be slit into eight individual ribbons. The ribbons of material are then be folded into a folded configuration such as a z-folded configuration. For example, each ribbon of material may define a top flap portion, a central portion and a bottom flap portion. The top and bottom flap portions are connected to and folded over and under the central portion, respectively to provide the z-folded configuration.

Each folded ribbon may then be combined, one ribbon on top of the other, with the other seven folded ribbons from the same web of material to form a continuous "sausage." The sausage is then cut into "clips" of eight wet wipes apiece and the clips of wet wipes are arranged in a stacked configuration. The number of clips in a stack depends on the desired number of stacks and the number of wet wipes in the final package. For example, for an 80-count package having one stack, ten clips of eight wet wipes apiece would be required to form a single stack of 80 wet wipes. After the stack of wet wipes is properly configured, it may be placed in the interior of a container, such as a plastic tub, to provide a package of wet wipes. The container provides a substantially hermetically sealed environment for the wet wipes to minimize the escape of any solution therefrom.

Accordingly, the different aspects of the present invention can advantageously provide wet wipes which, when compared to conventional wet wipes, have improved tactile properties and cleaning while maintaining low levels of skin irritation and foaming. Such wet wipes can advantageously be used for baby wipes, hand wipes, face wipes, cosmetic wipes, household wipes, industrial wipes and the like.

EXAMPLES

Example 1

A particularly suitable solution for the wet wipes of the present invention can be prepared according to the following formulation:

| Ingredient CTFA Designation | wt. % |
|---|---|
| Water | 96.905833 |
| Sunflower seedamidopropyl morpholine lactate | 2.600000 |
| Polysorbate 20 | 0.200000 |
| Tocopheryl acetate | 0.010000 |
| Sodium hydroxymethylglycinate | 0.200000 |
| Glycerin | 0.050000 |
| Aloe Barbadensis gel (200:1) | 0.002500 |
| Iodopropynyl butylcarbamate | 0.001667 |
| Fragrance | 0.030000 |

In preparing the foregoing solution, all materials are blended in a suitable mixing vessel at room temperature using agitation of approximately 50 rpm. Initially, the appropriate amount of water is added to a first mixing vessel, followed by the sunflower seedamidopropyl morpholine lactate. Thereafter the sodium hydroxymethylglycinate, glycerin, aloe barbadensis gel and the fragrance are added to the aqueous mixture. In a second mixing vessel, the following ingredients are combined in the following order and are allowed to mix completely (about 1 hour): Polysorbate 20 (sorbitan monolaurate with 20 mole percent ethoxylation); tocopheryl acetate; and iodopropynyl butylcarbamate. Thereafter, the contents of the second mixing vessel are added to the contents of the first mixing vessel to complete the formulation. The final pH is about 5.41.

To produce a wet wipe, the solution is then added to a fibrous substrate at an add-on of 330 percent of dry basis weight percent. The fibrous substrate can be a 72 grams per square meter coform basesheet having a pulpipolymer ratio of 68:32. The sheet size is about 19.0×19.0 centimeters. When in use, the resulting wet wipe imparts a soft, powdery feel to the skin and provides an improved moisture perception.

Example 2

An unscented formulation can be prepared as described in Example 1, but the fragrance component is eliminated.

Example 3

A pre-blend formulation for making a wet wipe is combined with water to provide the wet wipe of Example 1. The amount of the pre-blend formulation is about 3.1 weight percent when added to water to complete the formulation. The pre-blend formulation is formed by adding Polysorbate 20 to a mixing vessel. While gently stirring, tocopheryl acetate is added and allowed to mix until completely homogeneous. Iodopropynyl butylcarbamate is added to the Polysorbate 20 mixture while gently heating to 100° F. to aid dissolving the iodopropynyl butylcarbamate. Continue to stir until all of the iodopropynyl butylcarbamate is dissolved. The mixture is allowed to cool to 80° F. while stirring continues. The cationic fatty acid surfactant (such as sunflower seedamidopropyl morpholine lactate) is added while continuing stirring. The emulsification properties of the mixture allow the remaining ingredients to be added in any order. The resulting pre-blend has the following composition by weight percent:

| | |
|---|---|
| Sunflower seedamidopropyl morpholine lactate | 84.85 |
| Polysorbate 20 | 6.53 |

-continued

| | |
|---|---|
| Sodium hydroxymethylglycinate | 6.53 |
| Tocopheryl acetate | 0.33 |
| Glycerin | 1.63 |
| Aloe Barbadensis gel (200:1) | 0.08 |
| Iodopropynyl butylcarbamate | 0.05 |

The foregoing examples, given for purposes of illustration, are not to be construed as limiting the scope of this invention, which is defined by the following claims and all equivalents thereto.

We claim:

1. A wet wipe comprising a fibrousسheet material and an aqueous solution, said solution containing from about 0.01 to about 20 weight percent of a cationic fatty acid surfactant having a cationic nitrogen and a fatty acid moiety carbon chain length of from 8 to 40 wherein the cationic fatty acid surfactant comprises an organic counterion of sunflower seedamidopropyl morpholine.

2. The wet wipe of claim 1 wherein the cationic surfactant comprises a lactate or malate counterion.

3. The wet wipe of claim 1 wherein the aqueous solution contains a nonionic cosurfactant.

4. The wet wipe of claim 3 wherein the nonionic cosurfactant is selected from the group consisting of sorbitan monolaurate, sorbitan monoisostearate, sorbitan monopalmitate, lauramidodiethanolamide, alcohol ethoxylates and alkylphenol ethoxylates.

5. An aqueous solution containing from about 0.01 to about 20 weight percent of a cationic fatty acid surfactant having a cationic nitrogen and a fatty acid moiety carbon chain length of from 8 to 40 wherein the cationic fatty acid surfactant comprises an organic counterion of sunflower seedamidopropyl morpholine.

6. The aqueous solution of claim 5 wherein the cationic surfactant comprises a lactate or malate counterion.

7. The aqueous solution of claim 5 wherein the aqueous solution contains a nonionic cosurfactant.

8. The aqueous solution of claim 7 wherein the nonionic cosurfactant is selected from the group consisting of sorbitan monolaurate, sorbitan monoisostearate, sorbitan monopalmitate, lauramidodiethanolamide, alcohol ethoxylates and alkylphenol ethoxylates.

9. A wet wipe comprising a fibrous sheet material and an aqueous solution, said solution containing from about 0.01 to about 20 weight percent of a cationic fatty acid surfactant having a cationic nitrogen and a fatty acid moiety carbon chain length of from 8 to 40 wherein the cationic fatty acid surfactant comprises an organic counterion of sunflower seedamidopropyl dimethylamine.

10. The wet wipe of claim 9 wherein the cationic surfactant comprises a lactate or malate counterion.

11. The wet wipe of claim 9 wherein the aqueous solution contains a nonionic cosurfactant.

12. The wet wipe of claim 11 wherein the nonionic cosurfactant is selected from the group consisting of sorbitan monolaurate, sorbitan monoisostearate, sorbitan monopalmitate, lauramidodiethanolamide, alcohol ethoxylates and alkylphenol ethoxylates.

* * * * *